US00PP12323P2

(12) United States Plant Patent
Janick et al.

(10) Patent No.: US PP12,323 P2
(45) Date of Patent: Jan. 1, 2002

(54) APPLE TREE NAMED 'CO-OP 25'

(75) Inventors: Jules Janick, West Lafayette, IN (US); Schuyler S. Korban, Champaign, IL (US); Joseph Goffreda, Millstone, NJ (US)

(73) Assignee: Pursue Research Foundation, West Lafayette, IN (US)

( * ) Notice: Subject to any disclaimer, the term of this patent is extended or adjusted under 35 U.S.C. 154(b) by 0 days.

(21) Appl. No.: 09/204,925

(22) Filed: Dec. 3, 1998

(51) Int. Cl.[7] ..... A01H 5/00
(52) U.S. Cl. ..... Plt./161
(58) Field of Search ..... Plt./161, 165

(56) References Cited

U.S. PATENT DOCUMENTS

P.P. 6,588 * 2/1989 Hauenstein ..... Plt./161
P.P. 7,956 * 9/1992 Alston ..... Plt./161
P.P. 9,392 12/1995 Crosby et al. ..... Plt./172
P.P. 9,881 5/1997 Janick et al. ..... Plt./172

OTHER PUBLICATIONS http://www.applesource.com/marktdir.html, Jun. 2000.*

* cited by examiner

*Primary Examiner*—Bruce R. Campell
*Assistant Examiner*—Wendy C Baker
(74) *Attorney, Agent, or Firm*—Woodard, Emhardt, Naughton, Moriarty & McNett

(57) ABSTRACT

This invention is a new and distinct cultivar of apple tree (*Malus×domestica* Borkh.). The tree is a seedling of known parentage planted in May 1973 at the Clark Farm in West Lafayette, Ind., in the L Block, Row 20, Tree 41. When selected, it had the designation PRF 2714-4 in the breeding records and was tested under the designation "Co-op 25".

2 Drawing Sheets

BACKGROUND OF THE INVENTION

'Co-op 25' is a new and distinct cultivar of apple tree (*Malus×domestica* Borkh.), that was produced from crossing the selection PCFW 2-134 (unpatented) as the seed parent with the selection PRI 669-205 (unpatented) as the pollen parent in 1971 at the New Jersey Agricultural Experiment Station, Rutgers: The State University of New Jersey. The tree is a seedling of known parentage planted in May 1973 at the Clark Farm in West Lafayette, Ind. in the L Block, Row 20, Tree 41, hence its informal designation as CLR20T41. The seedling was selected as promising in 1978 and carried the progeny designation PRI 2714-4 in our breeding records. It was released for testing as Co-op 25 in 1984 and described in Purdue University Station Bulletin 456 (1984). FIG. 2 is a chart showing the complete pedigree of Co-op 25. This new cultivar is currently being sold under the trademark "SCARLET O'HARA".

This new cultivar carries the genetic factor $V_f$ inherited from *Malus floribunda* Sieb 821 that renders it highly resistant to the apple scab disease incited by *Venturia inaequalis*.(Cke.) Wint. Scab resistance was evaluated by controlled greenhouse inoculation tests at the seedling stage followed by twenty (20) years of observation under natural conditions for infection in the field in West Lafayette, Ind. and at multiple testing sites in the United States and abroad including sites in Italy, France, and Australia. Based on field observations, the selection is moderately susceptible to cedar apple rust incited by *Gymnosporanium juniperi-virginianae* (Schw.) and is moderately susceptible to mildew incited by *Podosphaera leucotricha* (Ell. & Ev.) Salm., and highly susceptible to fireblight incited by *Erwinia amylovora* (Burr.) Winslow, as well as moldy core, a fungal disease, of the seed cavity because of an open calyx, often due to Alternaria ssp.

This new cultivar produces a moderately vigorous, spreading tree which comes into bearing early. This tree is productive with fruit maturity one week before 'Delicious' (unpatented). Fruits averaging 80 mm in diameter weigh an average of about 201 g. The fruit is 90% medium red, up to 76 mm (3 inches) in diameter when well thinned, with very good dessert quality and excellent storage ability; the fruit typically exhibits the following characteristics: soluble solids=12.8%; penetrometer pressure=8.3 kg; titratable acidity=0.432 g malic acid equivalent/100 ml. The fruit is delicately spicy with a full flavor that combines sweetness and subacidity; very good, improves to best after 1 or more months in storage. After observation, the selection was asexually propagated by grafting to various rootstocks in Lafayette, Ind. and New Salisbury, Ind., and the grafted material has retained the described characteristics after propagation. The tree was selected when grown on its own roots and subsequently grown as grafted plants and tested in Indiana with seedling rootstock, Malling 7 (M.7) rootstock, and Malling-Merton 111(MM.111) rootstock. The new cultivar is precocious when grafted. The tree is considered diploid based on breeding behavior.

DETAILED DESCRIPTION OF THE NEW CULTIVAR

Figure 1:
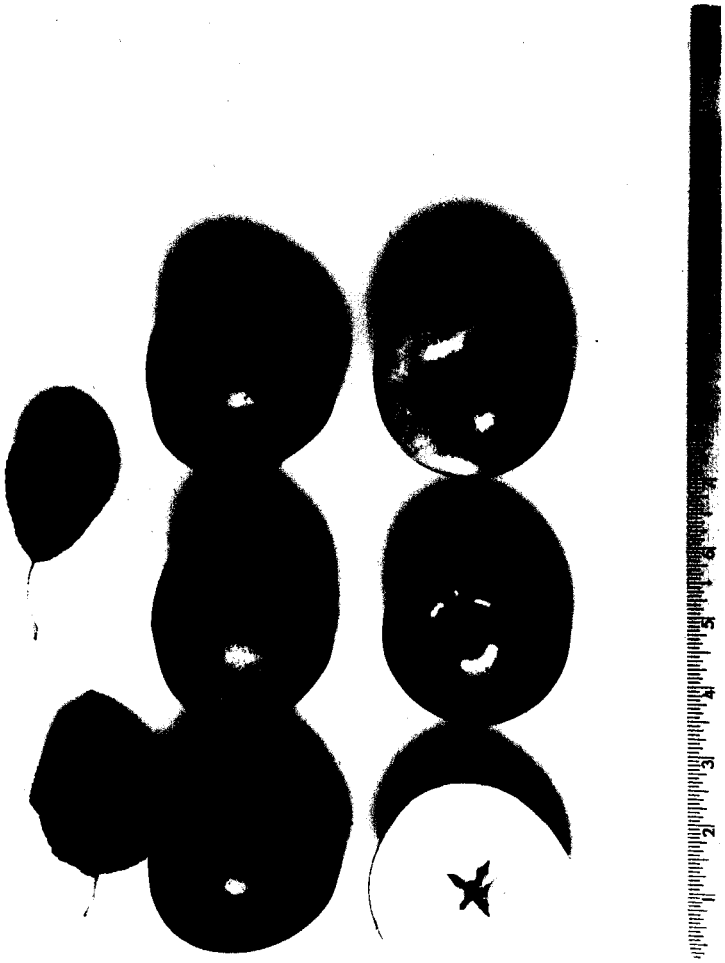
FIG. 1 is a photograph showing the fruit and leaves of Co-op 25.
Figure 2:
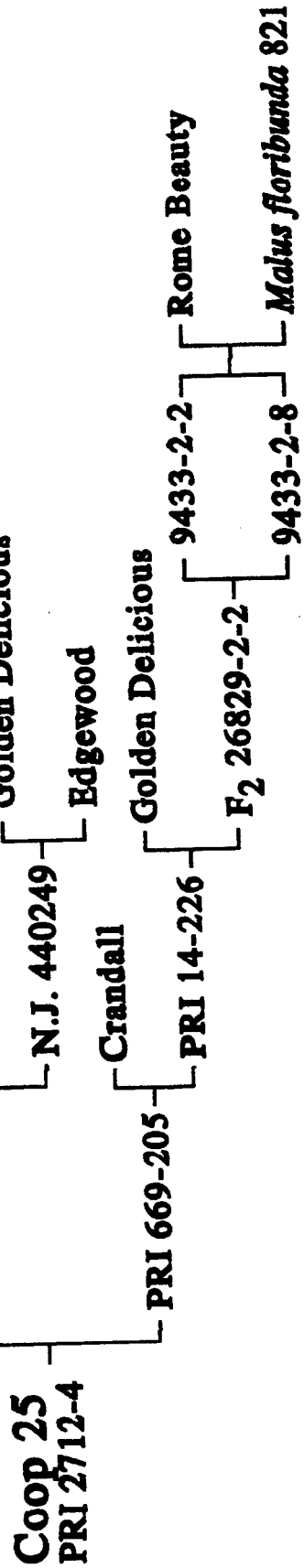
FIG. 2 is a chart showing the pedigree of Co-op 25.

The following is a detailed description of the new cultivar with color designations according to the 1966 Horticultural Colour Chart issued by The Royal Horticultural Society.

FLOWERS

Corolla: Average 43 mm in diameter at anthesis.
Petals: 14 mm×20 mm.
Color: Solferino Purple (Plate 26/1) in the bud, fading to Solferino Purple (Plate 26/3) to white in open flowers.
Season: Late, along with 'Rome Beauty' (unpatented); comparative bloom information obtained in Lafayette, Ind. in April 2000 is presented below:

| Cultivar | Bloom (% open) | |
|---|---|---|
| | April 20, 2000 | April 26, 2000 |
| Co-op 25 | 10 | 25 |
| Enterprise | 10 | 75 |
| Pristine (U.S. Pat. No. 6,268) | 25 | 75 |
| Williams' Pride (U.S. Pat. No. 9,881) | 50 | 95 |
| GoldRush | 75 | 95 |

Botanical features: Unopened flower bud Solferino Purple 26 to 26/3 and lighter as they open. There are 3 to 8 flowers per cluster, average 5.6, and 5 petals per flower. Pedicel length ranges from 20–28 mm, average 25.4 mm. When petals are open the color is white tinged with light purple on the outside, rarely inside. The petals range from 17–23 mm long (average 20.8 mm) and range from 11 to 15 mm wide (average 14.1 mm). The shape is elliptical. When fully open the flower diameter from petal tip to petal tip ranges from 39–49 mm, average 44.7 mm. When fully open the petals are barely touching to non-touching. Each flower has 20 stamens, white, 10 mm in length, with yellow anthers (Buttercup Yellow 5/2) in a single row. Pistil length is 10 mm, fused at base, Sap Green 62/2. Sepals are 7 mm long, 2 mm at base, recurved but not touching pedicel, Agathia Green 60/2 tinged with red, Magenta Rose 27/2.

FRUIT

Shape: Short-conic to round to slightly oblate, regular and slightly ribbed in cross section; slightly variable.
Size: Average diameter is 70 mm to 76 mm; length:width ratio=0.81.
Color: Undercolor is Chartreuse Green 663/1 to Indian Yellow (Plate 6/2) fading to Yellow Ochre (Plate o7/2); blushed overcolor, 60%–90% Currant Red (Plate 822/2 to 822/3).
Skin: Smooth, very slight wax, with inconspicuous tan to slightly russeted round dots; little tendency for russet, but occasional scarfing; medium thick but moderately tough; semi glossy, somewhat dull.
Stem: Average length 28 mm to 33 mm, moderately thin.
Cavity: Acute to obtuse, medium to shallow depth, medium width, smooth to russeted surface average height is 21 mm; average diameter is 24 mm.
Basin: Medium depth, medium breadth, rounded sides, smooth to wavy surface, glabrous average width is 25 mm; average depth is 7 mm; no protrusions.
Calyx: Persistent, open, lobes separated at base, narrowly lanceolate, accuminate, recurved.
Calyx tube: Conical to funnel-shaped; occasionally open to core cavity.
Stamens: Basal.
Core-lines: Clasping.
Core: Distant, open, medium.
Carpels: Round, emarginate to micronate cordate to round, ridged.
Seeds: Full complement, acute, non-tufted.
Flesh:
*Texture.*—Medium coarse-grained, firm, very crisp and breaking; maintains breaking texture in storage.
*Quality.*—Delicately spicy, full flavored, fruity, sweet, subacid; very good, improves to best after one or more months in storage.
*Color.*—Buttercup Yellow (Plane 5/3).
Maturity season: One week before 'Delicious', but remain firm and good tasting when left on the tree until the end of October in Lafayette, Ind. The average maturity date (eating ripe) of 'Delicious' in September 25 in Lafayette, Ind.
Keeping quality: Improves in storage and retains quality and texture at least seven months at 1° C.
Use: Dessert apple, appropriate for medium and long-term storage.

TREE

Vigor: Moderate, spreading. More vigorous than GoldRush (U.S. Plant Pat. No. 9,392) and less vigorous than Enterprise (U.S. Plant Pat. No. 9,193).
Shape: Spreading, round-topped.
Bearing habit: Some tendency for tip bearing but also bears on short shoots; develops bourse (purse-shaped) buds, tendency for more than on fruit per cluster; bearing limbs droop under fruit load; fruits are resistant to pre-harvest drop even when overripe; slight tendency for biennial bearing.
Branch angle: 45° to 90°.
Pollination requirements: Flowers are self-incompatible and set freely with various pollens when hybridized. The tree has not been found to be incompatible with any other cultivar.
Pruning/training requirements: Renewal pruning required because of tendency for bare wood on base of branches. Requirements similar to 'Rome Beauty'.
Productivity: Heavy, can overbear.
Thinning: Requires thinning to keep from overbearing.
Bark type and color: Current growth Maroon 1030 on distal portion. Basal portion to Willow Green 000862; the surface texture of the bark in the trunk of mature trees is Moderately Rough.
Stem: Current year stems are very pubescent; young shoots are Pea Green 61/2; mature shoots are Ruby Red 827 to 827/3; few lenticels, moderately conspicuous, rough, white; lenticels on two-year-old stems are larger, round, raised, tan, up to 1.6 mm; lenticels on three-year-old wood are elongated transversely, up to 1.6 mm×8 mm; lenticels on older stems are the same color as on bark, raised, corky, (6 mm×9.5 mm) and orange-tan.

LEAVES

Shape: Broadly ovate on new growth, ovate on older growth, compoundly serrate, occasionally simple serrate; average length is 100 mm; average width is 65 mm; average petiole is 30 mm; leaf tip is acuminate, leaf base is acute; leaves are pubescent.
Color: Upper surface Emerald Green (758); lower surface is Cyprus Green (59/1).

We claim:

1. A new and distinct apple tree as shown and described characterized by resistance to apple scab, precocious, high productivity, with good dessert quality based on flavor, crisp breaking flesh, and excellent storage ability.

* * * * *